US00PP24615P3

(12) United States Plant Patent
Schäfer

(10) Patent No.: US PP24,615 P3
(45) Date of Patent: Jul. 8, 2014

(54) VARIETY OF BASIL PLANT NAMED 'GREEN BALL'

(50) Latin Name: *Ocimum basilicum*
Varietal Denomination: Green Ball

(75) Inventor: Udo Schäfer, Wolsier (DE)

(73) Assignee: Herbalea GmbH, Grolsheim (DE)

( * ) Notice: Subject to any disclaimer, the term of this patent is extended or adjusted under 35 U.S.C. 154(b) by 125 days.

(21) Appl. No.: 13/385,809

(22) Filed: Mar. 7, 2012

(65) Prior Publication Data

US 2013/0239274 P1 Sep. 12, 2013

(51) Int. Cl.
*A01H 5/00* (2006.01)
*A01H 5/02* (2006.01)

(52) U.S. Cl.
CPC ..... *A01H 5/02* (2013.01)
USPC ..... Plt./258

(58) Field of Classification Search
CPC ..... A01H 5/02
USPC ..... Plt./258
See application file for complete search history.

(56) References Cited

U.S. PATENT DOCUMENTS

PP13,486 P2 * 1/2003 Bowden et al. ..... Plt./258
PP16,260 P2 * 2/2006 Bennerup ..... Plt./258

OTHER PUBLICATIONS

UPOV PLUTO QZ Citation for 'Green Ball' Feb. 15, 2011.*

* cited by examiner

*Primary Examiner* — Wendy C Haas
(74) *Attorney, Agent, or Firm* — The Webb Law Firm

(57) ABSTRACT

'Green Ball' is a new variety of non-flowering basil plant having a compact and rounded growth habit, high leaf production, and tolerance to low temperatures.

4 Drawing Sheets

Botanical classification: *Ocimum basilicum.*
Varietal denomination: 'GREEN BALL'.

CROSS REFERENCE TO RELATED APPLICATIONS

The new variety was discovered in the same cultivated area as basil plants named 'Ajaka', 'Dark Lady', and 'Green Fortune', each respectively claimed in U.S. Plant patent application Ser. Nos. 13/385,808, 13/385,798, and 13/385,811.

BACKGROUND OF THE NEW PLANT

The present invention comprises a new and distinct cultivar of basil plant, botanically known as *Ocimum basilicum* and hereinafter referred to by the cultivar name 'Green Ball'.

The new variety was discovered and selected by the breeder in a cultivated environment in July of 2009 in Wolsier, Germany (located in the region of Brandenburg) as a naturally occurring open-pollinated new variety in a population of unpatented and unnamed *Ocimum basilicum* plants. Subsequently, the new variety was asexually reproduced by cuttings in Wolsier, Germany in 2010. Further asexual reproductions at the same location has demonstrated that the combination of characteristics as herein disclosed for the new cultivar are retained and reproduced true to type through successive generations of asexual reproduction.

The following observations, measurements and comparisons describe 8-week-old plants grown in an open field with full sun, watered as needed, and receiving weekly fertilization treatments accented with nitrogen in Wolsier, Germany. The plants were exposed to daytime temperatures of 20-30° C., and evening temperatures of 10-20° C. Color observations were taken under natural light, and the color references are made to The R.H.S. Colour Chart of The Royal Horticulture Society of London, except where general color terms of ordinary significance are used.

The present invention has not been evaluated under all possible environmental conditions. The phenotype may vary with variation in environment without a change in the genotype of the plant.

The following traits have been repeatedly observed and determined to basic characteristics of 'Green Ball' which, in combination, distinguish this basil plant as a new and distinct cultivar:

1. Compact and rounded plant habit;
2. Sweet-spicy fragrance;
3. Aromatic taste;
4. Tolerant to Fusarium, Botrytis, and Pythium; and
5. Low temperature tolerance.

Further, the new variety exhibits a sweet-spicy fragance and aromatic taste like basil variety 'Dark Lady' (U.S. Plant patent application Ser. No. 13/385,798). However, 'Green Ball' has green leaves and a compact and rounded growth habit, while 'Dark Lady' has very dark violet leaves and tall growth habit. The following Table 1 provides a further comparative listing of botanical characteristics of 'Green Ball' and 'Dark Lady'.

TABLE 1

| Botanical characteristics | 'Green Ball' | 'Dark Lady' |
|---|---|---|
| Height from soil to top of plant: | 20 cm. | 50 cm. |
| Leaf length: | 2 cm. | 4.5 cm. |
| Number of leaves per plant: | Over 700 | About 200 |
| Flower production: | No | Yes |

BRIEF DESCRIPTION OF THE DRAWINGS

The accompanying photographic drawings illustrate the new variety, with the colors being as nearly true as is possible with color illustrations of this type.

DESCRIPTION OF THE PLANT

Figure 1:
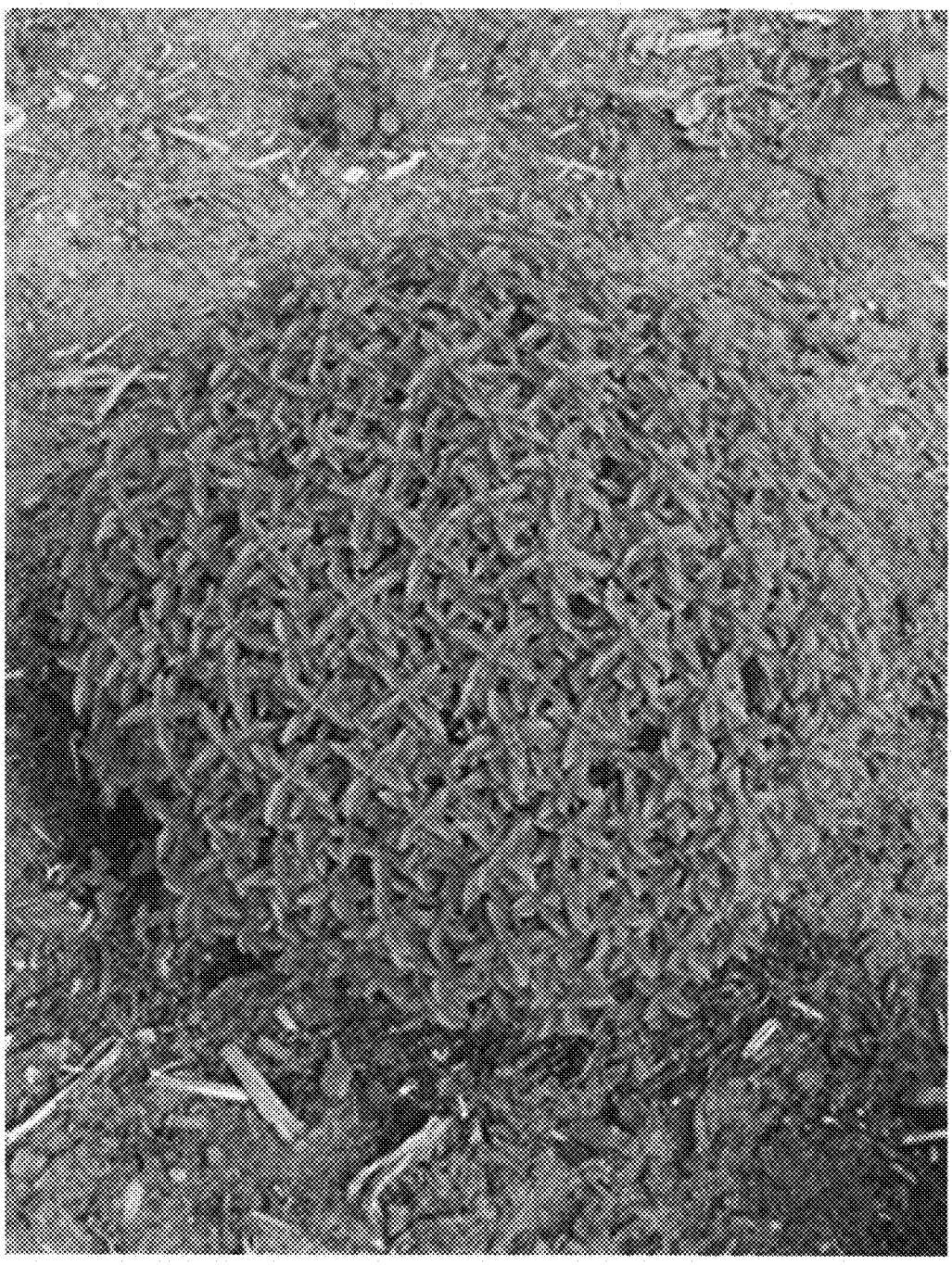
FIG. 1 is a photograph of the new variety in its entirety.
Figure 2:
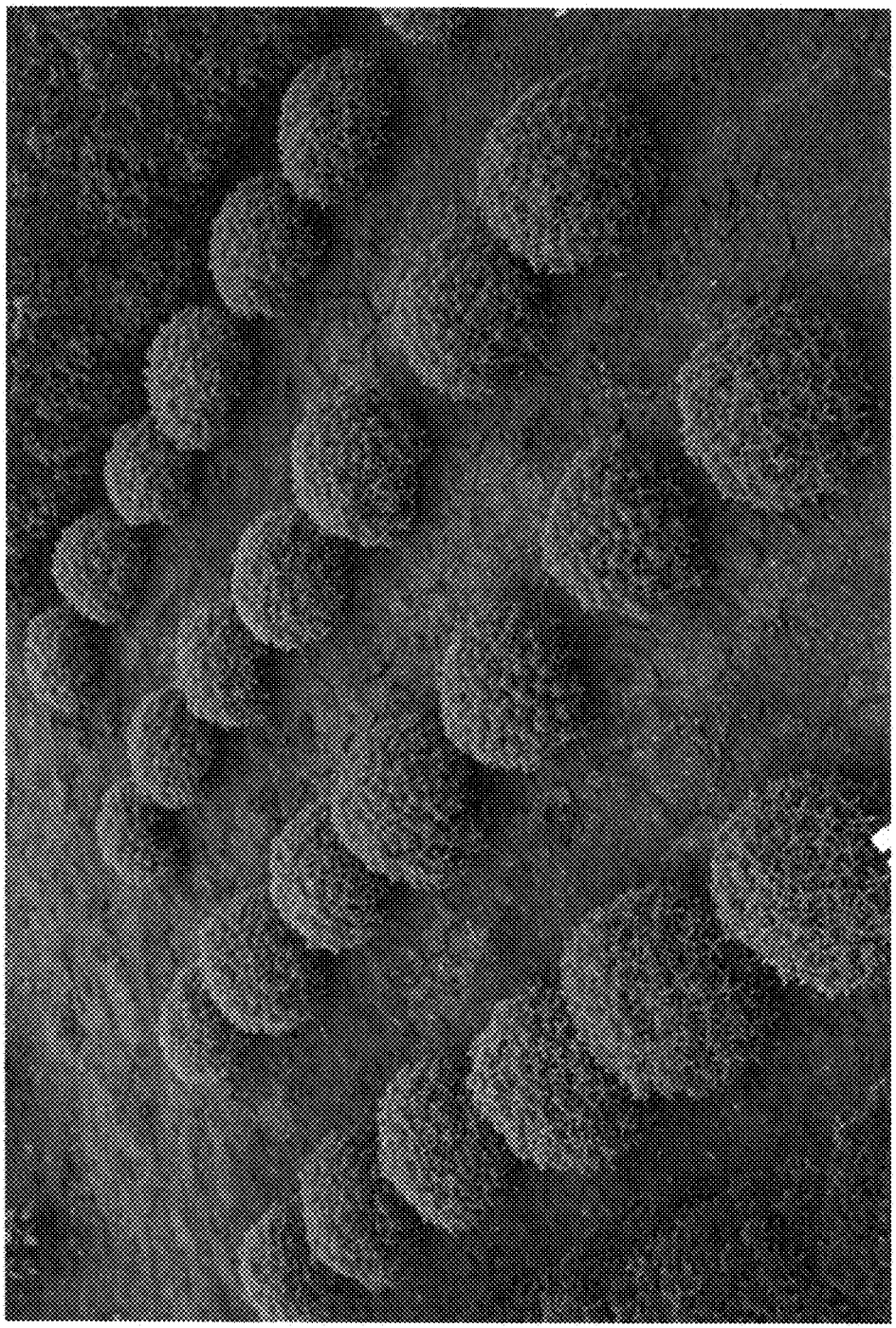
FIG. 2 is a photograph of a field of plants of the new variety.
Figure 3:
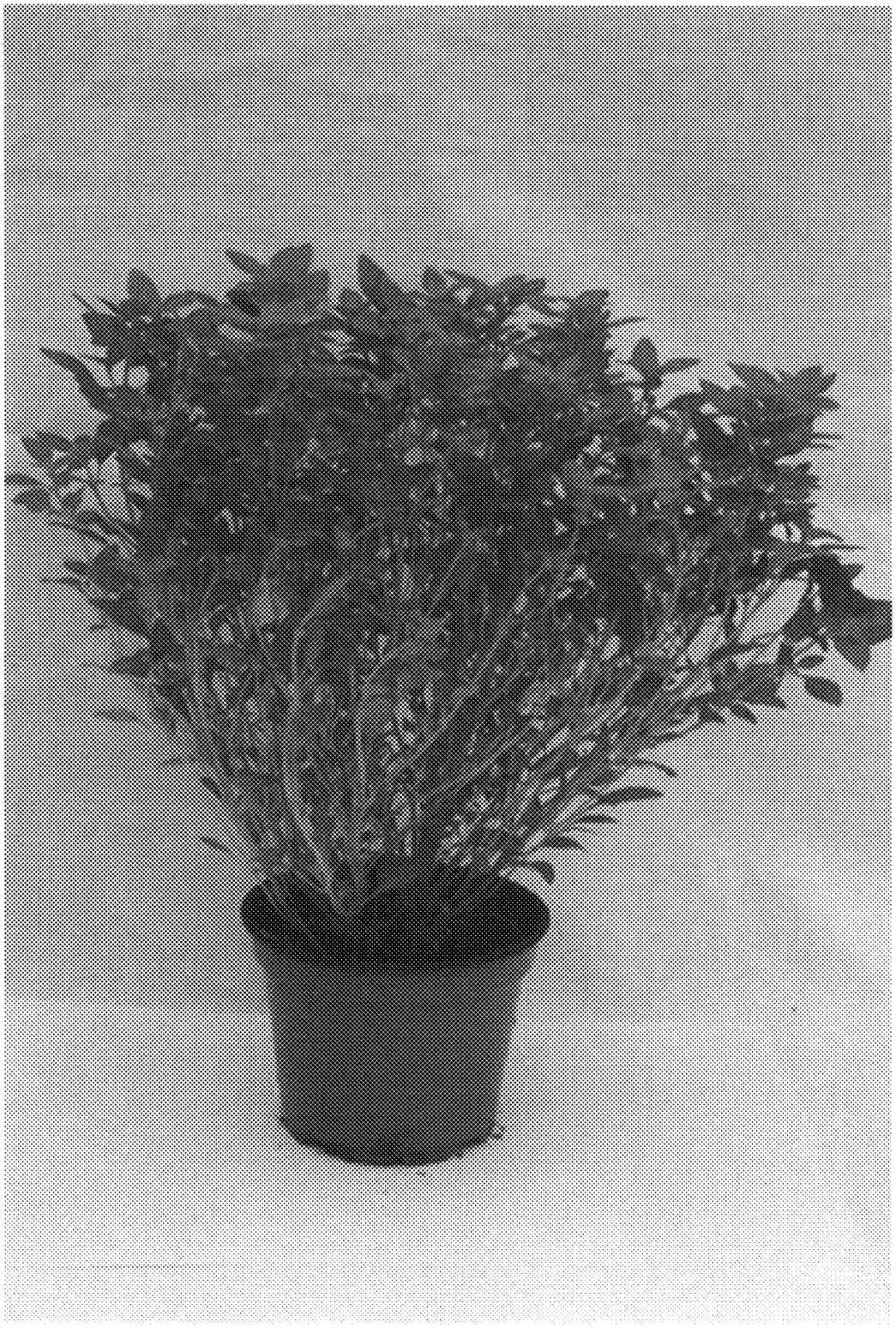
FIG. 3 is a photograph of the new variety when grown in a pot.
Figure 4:
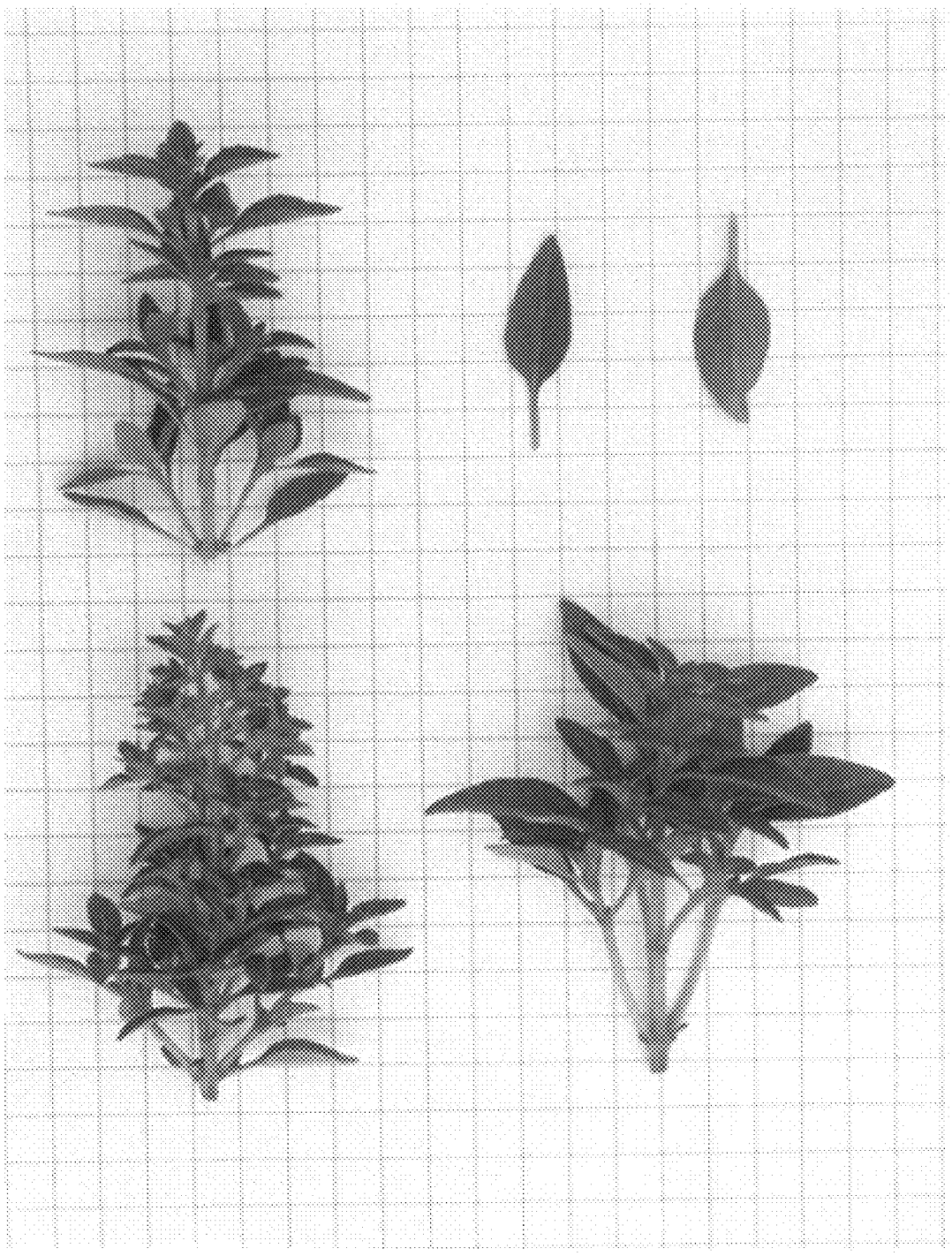
FIG. 4 is a photograph of the leaves and cuttings of the new variety.

Time to initiate roots: 5 days at 22° C.

Time to produce a rooted plant: 9 days at 22° C.

Root description: Finely branched white roots with a fibrous habit.

Form: Rounded.

Height from soil to top of plant: 20 cm.

Plant diameter: 25 cm.

Growth habit: Conglobate, round, with a very high-branching habit.

*Vigor*.—Weak, when compared to 'Wild Magic' (U.S. Plant patent application Ser. No. 13/385,805) and 'Habana' (U.S. Plant patent application Ser. No. 13/385,806).

Main stem:

*Length*.—30 cm.

*Width*.—0.5 cm.

*Color*.—Yellow-Green Group RHS 145A.

*Number of branches*.—30-40.

*Node spacing*.—1.5-3 cm.

Leaves:

*Arrangement*.—Decussate; pinnate.

*Number of leaves per plant*.—Over 700.

*Length*.—2 cm.

*Width*.—1 cm.

*Shape of leaf (generally)*.—Lanceolate.

*Shape of apex*.—Acute.

*Shape of base*.—Lanceolate.

*Texture*.—Nicely visible centreline from the petiole into the leaf. No pubescence is present.

*Aspect*.—Horizontal.

*Margin type*.—Shallow serration present.

*Upper surface color*.—Green Group RHS 137C.

*Lower surface color*.—Green Group RHS 137C.

*Veins*.—Upper surface description and color: Pinnate; Yellow-Green Group RHS 146C. Lower surface description and color: Pinnate; Green Group RHS 139C.

*Petiole*.—Length: 0.5-1.5 cm. Diameter: 1 mm. Color: Yellow-Green Group RHS 146C. Texture: Small hairs present. Shape: Round.

Reproductive organs: 1 pistil and 4 stamens present.

Flowers: 'Green Ball' is non-flowering.

Seed description: Sterile.

Disease/pest resistance: Tolerant to *Fusarium oxysporum*.

Weather tolerance: Very tolerant to rain and cold nights (down to 8° C.).

Harvesting season: Early summer to fall outdoors; year round indoors.

Flavor: Sweet-spicy.

Aroma: Spicy.

Essential oils: Linalool-eugenol-type.

Productivity/yield per acre:

*Fresh*.—4.9 tons per acre.

*Dried*.—0.7 tons per acre.

Average life span: 5 months.

Use: Multiple uses. The new variety can be used as a pot plant, ornamental plant, culinary herb, or fresh and dried herb.

Fresh shelf life: Over 1 week under cool conditions (5-8° C.).

I claim:

1. A new and distinct variety of basil plant named 'Green Ball' as herein described and illustrated.

* * * * *